(12) United States Patent
Zhang et al.

(10) Patent No.: US 7,767,825 B2
(45) Date of Patent: Aug. 3, 2010

(54) 2,2',6,6'-TETRAOXAZOLINYL BIPHENYL LIGAND AND METHOD FOR PREPARING THE SAME

(75) Inventors: Wanbin Zhang, Shanghai (CN); Yongjian Zhang, Shanghai (CN); Feijun Wang, Shanghai (CN)

(73) Assignee: Shanghai Jiaotong University, Shanghai (CN)

( * ) Notice: Subject to any disclaimer, the term of this patent is extended or adjusted under 35 U.S.C. 154(b) by 64 days.

(21) Appl. No.: 12/159,322

(22) PCT Filed: Dec. 29, 2006

(86) PCT No.: PCT/CN2006/003695

§ 371 (c)(1),
(2), (4) Date: Oct. 16, 2008

(87) PCT Pub. No.: WO2007/073698

PCT Pub. Date: Jul. 5, 2007

(65) Prior Publication Data

US 2009/0043104 A1    Feb. 12, 2009

(30) Foreign Application Priority Data

Dec. 29, 2005 (CN) ................... 2005 1 0112234

(51) Int. Cl.
C07D 263/08 (2006.01)
(52) U.S. Cl. .................................. 548/237
(58) Field of Classification Search .................. 548/237
See application file for complete search history.

(56) References Cited

OTHER PUBLICATIONS

Moorlag et al, "As Asymmetric Synthesis of a $C_2$ Symmetric Tetrasubstituted Biaryl: 2,2'-Dihydroxy-6,6'-Dimethyl-1,1'-Biphenyl, A Stable Chiral System," Tetrahedron Letters, vol. 34, No. 44, pp. 6993-6996, 1993.
Andrus et al., "Efficient Synthesis of 1,1'-Binaphthyl and 2,2'-Bi-o-tolyl-2,2'-bis(oxazoline)s and Preliminary Use of the Catalytic Asymmetric Allylic Oxidation of Cyclohexene," Journal of Organic Chemistry, vol. 62, No. 26, pp. 9365-9368, 1997.
Gant T.G. et al, "The First Enantioselective Synthesis of the Chemotactic Factor Sirenin by an Intramolecular [2+1] Cyclization Using a New Chiral Catalyst", Tetrahedron Letters, vol. 36, No. 48, pp. 8745-8748 (1995).
Imai Y. et al., "Novel Chiral Bisoxazoline Ligands with a Biphenyl Backbone: Preparation, Complexation, and Application in Asymmetric Catalytic Reactions", J. Org. Chem., vol. 65, pp. 3326-3333 (2000).
Imai Y. et al., "Novel Axial Chiral Catalyst Derived from Biphenyl Ligand Bearing only Two ortho-Substituents", Tetrahedron Letters, vol. 38, No. 15, pp. 2681-2684 (1997).
Qlao Z. et al., "Progress of Chiral Bis(oxazoline)-Metal Complexes Utilized in Asymmetric Cyclopropanation", Chinese Journal of Organic Chemistry, vol. 24, No. 1, pp. 15-22 (2004).
Bian Q.-H. et al., "Progress in Synthesis of Chiral Bis(oxaline) Ligands", Chinese Journal of Organic Chemistry, vol. 24, No. 12, pp. 1542-1552 (2004).
U.S. Appl. No. 12/159,440 to Wanbin Zhang et al., filed Jun. 27, 2008.

*Primary Examiner*—Kamal A Saeed
*Assistant Examiner*—Kristin Bianchi
(74) *Attorney, Agent, or Firm*—Greenblum & Bernstein, P.L.C.

(57) ABSTRACT

The present invention relates to a method for preparing 2,2',6,6'-tetraoxazolinyl biphenyl ligand in chemical industry field. In the present invention, compound (III) is reacted with an activator that can activate the hydroxyl group selected from the group consisting of alkyl halosulfonium compound, aryl halosulfonium compound, phosphoryl chloride, phosphorus pentachloride, thionyl chloride and triphenyl phosphine, in the presence of alkali(s), to give the target product (IV), 2,2',6,6'-tetraoxazolinyl biphenyl ligand. The ligand of the present invention can be used in various asymmetric reactions catalyzed by metals, with high reactivity and stereoselectivity, and thus represents a good application outlook. The 2,2',6,6'-tetraoxazolinyl biphenyl ligand has the formula of:

(IV)

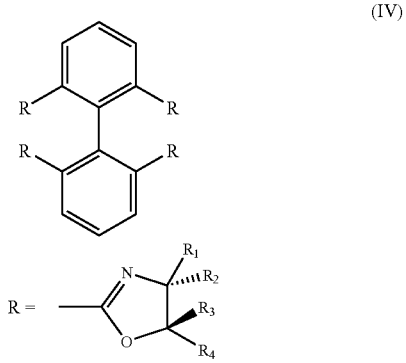

wherein, $R_1$=hydrogen, alkyl, substituted or unsubstituted aryl, substituted or unsubstituted benzyl; $R_2$=hydrogen, alkyl, substituted or unsubstituted aryl, substituted or unsubstituted benzyl; $R_3$=hydrogen, alkyl, substituted or unsubstituted aryl, substituted or unsubstituted benzyl; $R_4$=hydrogen, alkyl, substituted or unsubstituted aryl, substituted or unsubstituted benzyl.

6 Claims, No Drawings

2,2',6,6'-TETRAOXAZOLINYL BIPHENYL LIGAND AND METHOD FOR PREPARING THE SAME

TECHNICAL FIELD

The present invention relates to a compound in chemical industry field and its preparation method, more specifically, to 2,2',6,6'-tetraoxazolinyl biphenyl ligand and its preparation method.

BACKGROUND

Oxazoline is a five-membered heterocyclic compound containing N and O atoms, wherein the atom of N can coordinate with metal ions as a donor atom. Further, oxazoline can be used as substrate to synthesize various chiral compounds with great success, which makes the chemists believe that oxazoline represents a good outlook in asymmetric catalysis as a ligand. During the past 30 years, a large numbers of chiral oxazoline ligands have been developed, especially those with various chiral side chains. Among others, axial chiral side chain has been widely used in the ligand due to its unique rigid structure. In order to obtain an axial chiral ligand with single configuration, the prior art mainly applies a resolution method or the like, which results in a great extent of waste in resources.

After searching in the prior art, Professor Imai, et. al. (*J. Org. Chem.*, 65, 3326-3333, "Novel Chiral Bisoxazoline Ligands with a Biphenyl Backbone: Preparation, Complexation, and Application in Asymmetric Catalytic Reactions") reported that an axis unstable ligand 1 adopts two interchanging forms of (S,aS,S)-1 and (S,aR,S)-1 in a solution, while only the (S,aS,S)-1 chelates with a metal salt ion to form an axial chiral ligand compound (S,aS,S)-2, as confirmed through chelating with a metal salt ion. Such an axial chiral ligand compound can be easily synthesized without complicated resolution process. In addition, (S,aS,S)-2 obtains certain enantioselectivity during the asymmetric cyclopropylation reaction that involves the catalysis of olefin. Its disadvantage lies in that: such a ligand is still an axial chiral ligand which is unstable in the axial chirality, and thus it does not break through the design concept of an axial chiral ligand.

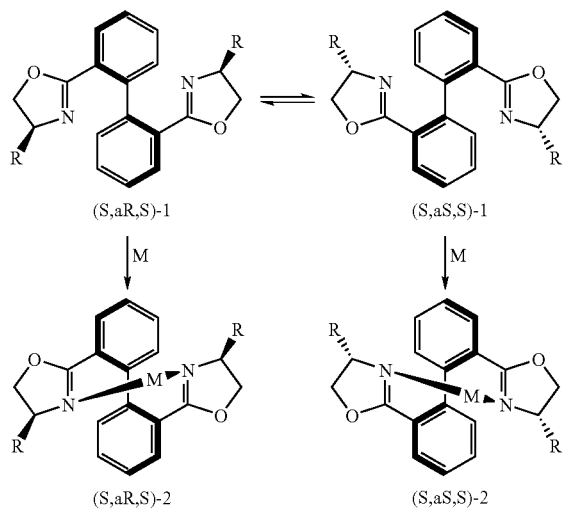

SUMMARY OF THE INVENTION

The object of the present invention is to provide a 2,2',6,6'-tetraoxazolinyl biphenyl ligand and its preparation method, so as to resolve the problems of waste in resources and the like in the prior art of preparation of single axial chiral ligands. In addition, the synthesis method is simple, and the ligand prepared can be used to prepare the catalyst for an asymmetric catalytic reaction.

The present invention is carried out through the following technical solution. The 2,2',6,6'-tetraoxazolinyl biphenyl ligand of the present invention has the following formula:

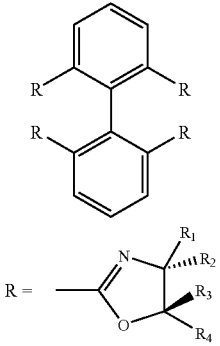

$R_1$=hydrogen, alkyl, substituted or unsubstituted aryl, substituted or unsubstituted benzyl;

$R_2$=hydrogen, alkyl, substituted or unsubstituted aryl, substituted or unsubstituted benzyl;

$R_3$=hydrogen, alkyl, substituted or unsubstituted aryl, substituted or unsubstituted benzyl;

$R_4$=hydrogen, alkyl, substituted or unsubstituted aryl, substituted or unsubstituted benzyl.

wherein, the alkyl group of $R_1$-$R_4$ is preferably $C_1$-$C_8$ straight or branched alkyl; the aryl group is preferably phenyl, tosyl, xylyl, or naphthoyl. In addition, the above aryl and benzyl groups are optionally substituted by substitutes selected from alkyl, hydroxy, alkoxy, and halogen.

The above 2,2',6,6'-tetraoxazolinyl biphenyl ligand of the present invention can be prepared by the method comprising: reacting the compound of formula (III) with an activator that can activate the hydroxyl group selected from the group consisting of alkyl halosulfonium compound, aryl halosulfonium compound, phosphoryl chloride, phosphorus pentachloride, thionyl chloride and triphenyl phosphine, in the presence of alkali(s) (described in details in the following step (4)). Further, the compound of formula (III) is preferably the substance obtained by the following steps (1)-(3).

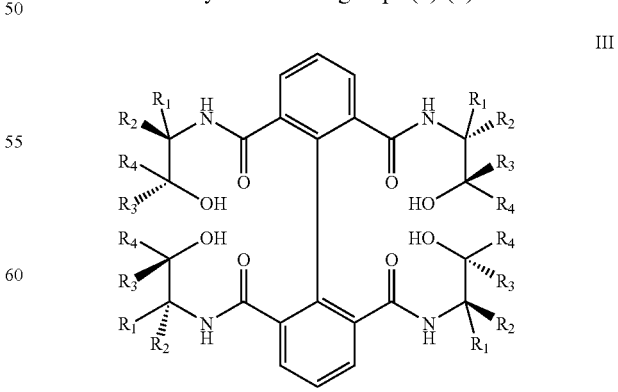

(wherein, $R_1$, $R_1$, $R_4$, $R_4$ are defined as above.)

Further, compounds (I)-(IV) of the present invention have the formulae as below.

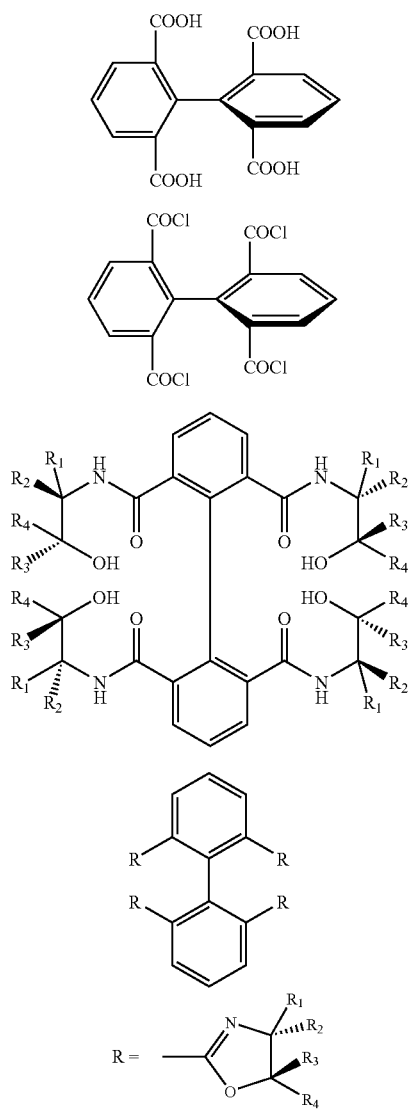

In above formulae, $R_1$, $R_1$, $R_4$, $R_4$ are defined as above.

Step (1): Synthesis of Compound (I) Using Pyrene as the Starting Material

In a oxidation system of sodium periodate and ruthenium trichloride, pyrene is ring-opening oxidized in solvent(s) to synthesize 2,2',6,6'-tetracarboxy biphenyl (I).

The reaction conditions are: the molar ratio of pyrene and sodium periodate is 1:5-15, the molar ratio of pyrene and ruthenium trichloride is 1:0.01-0.1, the reaction temperature is 10-50° C., and the reaction time is 12-25 hrs.

The examples of the solvent(s) are esters, such as methyl formate, ethyl formate, methyl acetate, ethyl acetate, butyl acetate, ethyl propionate, and the like; halohydrocarbons, such as dichloromethane, trichloromethane, carbon tetrachloride, dichloroethane, dibromoethane, chlorobenzene, and the like; ethers, such as diethyl ether, dibutyl ether, 1,4-dioxane, tetrahydrofuran, and the like; carbonitriles, such as acetonitrile, butyronitrile, and the like; hydrocarbons, such as pentane, hexane, cyclohexane, and the like; etc. The solvent may be used alone, or two or more solvents may be used in combination.

Step (2): Synthesis of Compound (II) Using Compound (I) as the Starting Material The compound (I) is reacted with thionyl chloride in organic solvent(s) to synthesize the acyl chloride (II).

The reaction conditions are: the molar ratio of compound (I) and thionyl chloride is 1:3-6, the reaction temperature is 10-100° C., and the reaction time is 1-20 hrs.

The examples of the organic solvent are lower halohydrocarbons, such as trichloromethane, dichloromethane, dichloroethane, carbon tetrachloride, and the like; aromatic hydrocarbons, such as benzene, chlorobenzene, and the like; di-(lower alkyl) ethers, such as diethyl ether, dimethyl ether, and the like; cyclic ethers, such as tetrahydrofuran, 1,4-dioxane, and the like; lower dialkoxy ethane, such as 1,2-dimethoxyethane, 1,2-diethoxyethane, 1,2-dibutoxyethane, 1,2-dihexyloxyethane, and the like; aliphatic amides, such as dimethyl formamide, and the like. The organic solvent may be used alone, or two or more organic solvents may be used in combination.

Step (3): Synthesis of Compound (III) Using Compound (II) as the Starting Material In organic solvent(s), acyl chloride (II) is reacted with an amino alcohol in the presence of alkali(s) to synthesize compound (III).

The reaction conditions are: the molar ratio of acyl chloride (II) and amino alcohol is 1:4-6, the reaction temperature is 0-80° C., and the reaction time is 4-25 hrs.

Said amino alcohol is

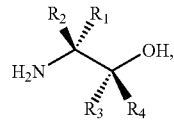

wherein $R_1$, $R_2$, $R_3$, $R_4$ are defined as above.

The examples of the alkali are metal hydrides, such as sodium hydride, and the like; amines, such as trimethylamine, triethylamine, diisopropyl ethylamine, and the like; alkali hydroxides, such as potassium hydroxide, sodium hydroxide, and the like; alkali carbonates, such as sodium carbonate, potassium carbonate, and the like; alkoxides, such as sodium methoxide, potassium methoxide, sodium ethoxide, potassium ethoxide, and the like; piperidine; pyridine; potassium cresol; lithium alkylide; 1,8-diazobicyclo[5,4,0]hendec-7-ene; lithium bis(trimethylsilyl)amide; etc. The alkali may be used alone, or two or more alkalis may be used in combination.

The examples of the organic solvent are esters, such as methyl formate, ethyl formate, methyl acetate, ethyl acetate, butyl acetate, ethyl propionate, and the like; halohydrocarbons, such as dichloromethane, trichloromethane, carbon tetrachloride, dichloroethane, dibromoethane, chlorobenzene, and the like; ethers, such as diethyl ether, dibutyl ether, 1,4-dioxane, tetrahydrofuran, and the like; carbonitriles, such as acetonitrile, butyronitrile, and the like; hydrocarbons, such as pentane, hexane, cyclohexane, and the like; etc. The solvent may be used alone, or two or more solvents may be used in combination.

Step (4): Synthesis of Compound (IV) Using Compound (III) as the Starting Material.

In organic solvent(s), compound (III) is reacted with an activator that can activate the hydroxyl group selected from the group consisting of alkyl halosulfonium compound, aryl halosulfonium compound, phosphoryl chloride, phosphorus pentachloride, thionyl chloride and triphenyl phosphine, in the presence of alkali(s), to synthesize 2,2',6,6'-tetraoxazolinyl biphenyl ligand (IV). The reaction conditions are: the molar ratio of compound (III), alkali and activator is 1:5-12: 4-10, the reaction temperature is 0-80° C., and the reaction time is 1-25 hrs.

The alkali is not particularly limited. The examples of alkali include, but are not limited to, metal hydrides, such as sodium hydride, and the like; amines, such as trimethylamine, triethylamine, diisopropyl ethylamine, and the like; alkali hydroxides, such as potassium hydroxide, sodium hydroxide, and the like; alkali carbonates, such as sodium carbonate, potassium carbonate, and the like; alkoxides, such as sodium methoxide, potassium methoxide, sodium ethoxide, potassium ethoxide, and the like; piperidine; pyridine; potassium cresol; lithium alkylide; 1,8-diazobicyclo[5,4,0]hendec-7-ene; lithium bis(trimethylsilyl)amide; etc. The alkali may be used alone, or two or more alkalis may be used in combination.

Further, as the activator, alkyl halosulfonium compounds, such as methane sulfonyl chloride, and the like; aryl halosulfonium compounds, such as benzene sulfonyl chloride, p-toluene sulfonyl chloride, and the like; phosphoryl chloride; phosphorus pentachloride; thionyl chloride; and triphenyl phosphine can be used.

The examples of the organic solvent are esters, such as methyl formate, ethyl formate, methyl acetate, ethyl acetate, butyl acetate, ethyl propionate, and the like; halohydrocarbons, such as dichloromethane, trichloromethane, carbon tetrachloride, dichloroethane, dibromoethane, chlorobenzene, and the like; ethers, such as diethyl ether, dibutyl ether, 1,4-dioxane, tetrahydrofuran, and the like; carbonitriles, such as acetonitrile, butyronitrile, and the like; hydrocarbons, such as pentane, hexane, cyclohexane, and the like; etc. The solvent may be used alone, or two or more solvents may be used in combination.

The present invention can resolve the problems of waste in resources and the like in the prior art of preparation of single axial chiral ligands. In addition, the synthesis method is simple. The 2,2',6,6'-tetraoxazolinyl biphenyl ligand of the present invention incorporates both the central chirality oxazoline and the axial chirality of diphenyls. Such ligand can be used in various asymmetric reactions catalyzed by metal, such as asymmetric cyclopropylation reaction, intramolecular Wacker-Type cyclization reaction, asymmetric oxidation reaction of olefin, and intramolecular [2+1] ring addition reaction, and the like, with high reactivity and stereoselectivity, and thus represents a good application outlook.

EMBODIMENTS OF THE INVENTION

The following examples are provided for illustration of the present invention, rather than the limitation of the present invention.

Further, the synthesis route of the examples is as follows:

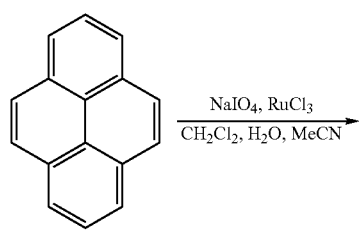

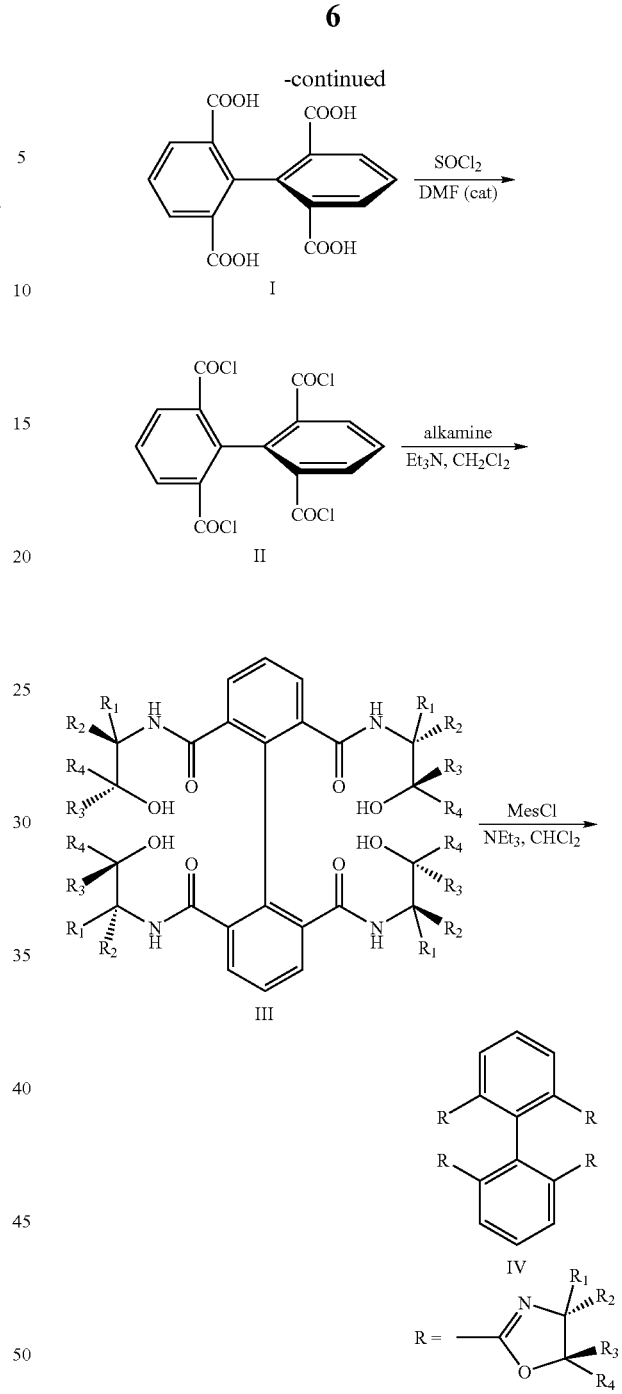

Example 1

(1) Synthesis of Compound (I)

Pyrene (3.00 g, 14.90 mmol) is dissolved in mixed solvents of dichloromethane (60 mL), acetonitrile (60 mL) and water (100 mL). Sodium periodate (29.94 g, 140 mmol) and ruthenium trichloride (120.31 g, 0.58 mmol) are added into above solution. After the reaction solution is heated to 40° C. and stirred for 16 hrs, yellow precipitate comes out. The solid obtained by filtration is dissolved in acetone (200 mL), and the insoluble substances are filtered out. The filtrate is condensed via rotary evaporation to give white powder (I) (2.30 g, 76%).

¹H NMR (400 MHz, CD$_3$COCD$_3$) 6.99 (d, J=7.6 Hz, 4H, Ar—H), 6.77 (t, J=7.6 Hz, 2H, Ar—H).

(2) Synthesis of Compound (II)

Tetra acid (I) (1.00 g, 3.03 mmol) is dissolved in dichloromethane (20 mL). The solution is added with thionyl chloride (1.0 mL, 13.34 mmol) and 16 μL DMF in an ice bath. The reaction temperature is allowed to reach the room temperature. After stirring for 1 hr at r.t., the reaction is heated in reflux until the reaction solution becomes homogenous (~5 hr). After heating in reflux for another 1 hr, the orange solution is condensed to give solid (II) (yield 90%).

¹H NMR (400 MHz, CDCl$_3$) 8.539 (d, J=8.0 Hz, 2H, Ar—H), 7.803 (t, J=8.0 Hz, 1H, Ar—H).

(3) Synthesis of Compound (III) ($R_1$=i-Pr, $R_2$=$R_3$=$R_4$=H)

(II) (1.28 g, 3.16 mmol) is dissolved in dichloromethane (40 mL) in an ice bath. The resultant solution is added dropwise into the solution of L-valinol (1.96 g, 14.88 mmol) in dichloromethane (20 mL). After the addition, triethylamine (2.4 mL, 17.28 mmol) is added quickly. After stirring for 20 hrs at r.t., the mixture is washed with water and filtered to give amide compound (III) ($R_1$=i-Pr, $R_2$=$R_3$=$R_4$=H) (1.70 g, 2.53 mmol) with a yield of 80%.

¹H NMR (400 MHz, CD$_3$OD) 7.48-7.52 (m, 6H, Ar—H), 3.574-3.617 (m, 4H, NCH), 3.46 (dd, J=6.4, 11.6 Hz, 4H, OCH), 3.39 (dd, J=4.4, 11.6 Hz, 4H, OCH), 1.65-1.77 (m, 4H, Me$_2$CH), 0.72 (d, J=2.4 Hz, 12H, CH$_3$), 0.71 (d, J=2.4 Hz, 12H, CH$_3$).

(4) Synthesis of Compound (IV) ($R_1$=i-Pr, $R_2$=$R_3$=$R_4$=H)

Methyl sulfonyl chloride (0.7 mL, 8.96 mmol) is added dropwise into the mixture of amide compound (III) ($R_1$=i-Pr, $R_2$=$R_3$=$R_4$=H) (1.0 g, 1.49 mmol), triethylamine (1.3 mL, 9.32 mmol) and dichloromethane (10 mL). After stirring for 12 hrs at r.t., the reaction mixture is diluted with dichloromethane (10 mL). The organic layer is washed with water. After drying over anhydrous magnesium sulfate, the solution is rotatory evaporated to give crude product. The crude product is purified thought column chromatograph with ethyl acetate and petroleum ether (1:3) as the eluent, to give compound (IV) (0.53 g, 0.88 mmol) with a yield of 59%.

¹H NMR (400 MHz, CDCl$_3$) 7.89 (d, J=8.0 Hz, 4H, Ar—H), 7.34 (d, J=7.6 Hz, 2 H, Ar—H), 3.98 (dd, J=7.6, 9.2 Hz, 4H, NCH), 3.67-3.77 (m, 8H, OCH$_2$), 1.52-1.60 (m, 4H, Me$_2$CH), 0.76 (d, J=6.8 Hz, 12H, CH$_3$), 0.73 (d, J=6.8 Hz, 12H, CH$_3$).

The synthesis method of the Example is simple and results in a yield. The result axial chiral ligand may coordinate with metal ions, such as copper, palladium and the like, to form an axial chiral ligand compound. The preparation of the axial chiral ligand compound does not need the complicated separation means, such as resolution.

Example 2

(1) Synthesis of Compound (I)

The synthesis method refers to (1) of Example 1.

(2) Synthesis of Compound (II)

The synthesis method refers to (2) of Example 1.

(3) Synthesis of Compound (III) ($R_1$=i-Pr, $R_2$=$R_3$=$R_4$=H)

(II) (1.01 g, 2.49 mmol) is dissolved in dichloromethane (30 mL) in an ice bath.

The resultant solution is added dropwise into the solution of L-valinol (1.97 g, 14.88 mmol) in dichloromethane (20 mL). After the addition, triethylamine (2.4 mL, 17.28 mmol) is added quickly. After stirring for 20 hrs at r.t., the mixture is washed with water and filtered to give amide compound (III) ($R_1$=i-Pr, $R_2$=$R_3$=$R_4$=H) (1.44 g, 2.14 mmol) with a yield of 86%.

(4) Synthesis of Compound (IV) ($R_1$=i-Pr, $R_2$=$R_3$=$R_4$=H)

Methyl sulfonyl chloride (1.2 mL, 14.86 mmol) is added dropwise into the mixture of amide compound (III) ($R_1$=i-Pr, $R_2$=$R_3$=$R_4$=H) (1.0 g, 1.49 mmol), triethylamine (2.5 mL, 17.67 mmol) and dichloromethane (10 mL). After stirring for 5 hrs at r.t., the reaction mixture is diluted with dichloromethane (10 mL). The organic layer is washed with water. After drying over anhydrous magnesium sulfate, the solution is rotatory evaporated to give a crude product. The crude product is purified thought column chromatograph with ethyl acetate and petroleum ether (1:3) as the eluent, to give compound (IV) (0.56 g, 0.93 mmol) with a yield of 62%.

Example 3

(1) Synthesis of Compound (I)

The synthesis method refers to (1) of Example 1.
(2) Synthesis of Compound (II)
The synthesis method refers to (2) of Example 1.

(3) Synthesis of Compound (III) ($R_1$=t-Bu, $R_2$=$R_3$=$R_4$=H)

(II) (1.00 g, 2.46 mmol) is dissolved in dichloromethane (40 mL) in an ice bath. The resultant solution is added dropwise to the solution of L-t-butyl leucinol (1.44 g, 12.30 mmol) in dichloromethane (20 mL). After the addition, triethylamine (1.8 mL, 12.96 mmol) is added quickly. After stirring for 20 hrs at r.t., the mixture is washed with water and filtered to give amide compound (III) ($R_1$=t-Bu, $R_2$=$R_3$=$R_4$=H) (1.51 g, 2.08 mmol) with a yield of 84%.

¹H NMR (400 MHz, CD$_3$OD) 7.46-7.52 (m, 6H, Ar—H), 3.69-3.74 (m, 8H, NCH, OCH), 3.37 (dd, J=10.8, 12.8 Hz, 4H, OCH), 0.734 (s, 36H, CH$_3$).

(4) Synthesis of Compound (IV) ($R_1$=t-Bu, $R_2$=$R_3$=$R_4$=H)

Methyl sulfonyl chloride (0.5 mL, 6.90 mmol) is added dropwise into the mixture of amide compound (III) ($R_1$=t-Bu, $R_2$=$R_3$=$R_4$=H) (1.0 g, 1.38 mmol), triethylamine (1.2 mL, 8.60 mmol) and dichloromethane (10 mL). After stirring for 12 hrs at r.t., the reaction mixture is diluted with dichloromethane (10 mL). The organic layer is washed with water. After drying over anhydrous magnesium sulfate, the solution is rotatory evaporated to give a crude product. The crude product is purified thought column chromatograph with ethyl acetate and petroleum ether (1:3) as the eluent, to give compound (IV) (0.48 g, 0.73 mmol) with a yield of 53%.

$^1$H NMR (400 MHz, CDCl$_3$) 7.92 (d, J=7.6 Hz, 4H, Ar—H), 7.34 (d, J=8.0 Hz, 2 H, Ar—H), 3.91 (dd, J=12.0, 13.2 Hz, 4H, NCH), 3.68-3.73 (m, 8H, OCH), 0.664 (s, 36 H, CH$_3$).

The invention claimed is:

1. A 2,2',6,6'-tetraoxazolinyl biphenyl ligand, characterized in that said 2,2',6,6'-tetraoxazolinyl biphenyl ligand has the formula of:

(IV)

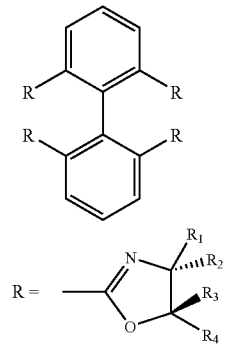

wherein, R$_1$=hydrogen, alkyl, substituted or unsubstituted aryl, substituted or unsubstituted benzyl;

R$_2$=hydrogen, alkyl, substituted or unsubstituted aryl, substituted or unsubstituted benzyl;

R$_3$=hydrogen, alkyl, substituted or unsubstituted aryl, substituted or unsubstituted benzyl;

R$_4$=hydrogen, alkyl, substituted or unsubstituted aryl, substituted or unsubstituted benzyl.

2. A method for preparing 2,2',6,6'-tetraoxazolinyl biphenyl ligand, characterized in that said method is a method for preparing 2,2',6,6'-tetraoxazolinyl biphenyl ligand of formula (IV) comprising:

reacting the compound of formula (III) with an activator that can activate the hydroxyl group selected from the group consisting of alkyl halosulfonium compound, aryl halosulfonium compound, phosphoryl chloride, phosphorus pentachloride, thionyl chloride and triphenyl phosphine, in the presence of alkali(s), to give the resultant (IV), 2,2',6,6'-tetraoxazolinyl biphenyl ligand,

III

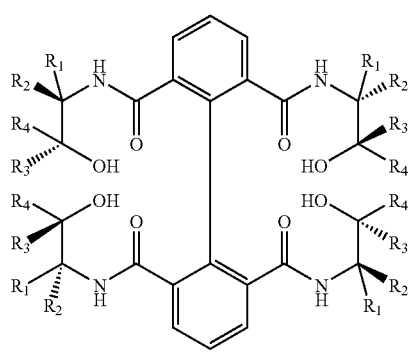

wherein R$_1$, R$_2$, R$_3$, R$_4$ are defined as above.

3. A method for preparing 2,2',6,6'-tetraoxazolinyl biphenyl ligand, characterized in that said method is a method for preparing 2,2',6,6'-tetraoxazolinyl biphenyl ligand of formula (IV) comprising:

in a oxidation system of sodium periodate and ruthenium trichloride, pyrene is ring-opening oxidized to to give 2,2',6,6'-tetracarboxy biphenyl (I), then, in organic solvent(s), the 2,2',6,6'-tetracarboxy biphenyl (I) is reacted with thionyl chloride to give an acyl chloride (II), then, in organic solvent(s), the acyl chloride (II) is reacted with an amino alcohol in the presence of alkali(s) to give a product (III), then, in the presence of alkali(s), the product (III) is reacted with an activator that can activate the hydroxyl group selected from the group consisting of alkyl halosulfonium compound, aryl halosulfonium compound, phosphoryl chloride, phosphorus pentachloride, thionyl chloride and triphenyl phosphine.

4. The method for preparing 2,2',6,6'-tetraoxazolinyl biphenyl ligand according to claim 3, characterized in that, in the reaction of obtaining of compound (III) from compound (II), the molar ratio of compound (II) and the amino alcohol is 1:4-6, the reaction temperature is 0-80° C., and the reaction time is 4-25 hrs.

5. The method for preparing 2,2',6,6'-tetraoxazolinyl biphenyl ligand according to claim 3, characterized in that, in the reaction of obtaining compound (IV) from compound (III), the molar ratio of compound (III), the alkali(s) and the activator is 1:5-12:4-10, the reaction temperature is 0-80° C., and the reaction time is 1-25 hrs.

6. The method for comprising 2,2',6,6'-tetraoxazolinyl biphenyl ligand according to claim 3, characterized in that, the amino alcohol is

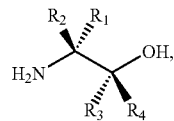

wherein, R$_1$=hydrogen, alkyl, substituted or unsubstituted aryl, substituted or unsubstituted benzyl;

R$_2$=hydrogen, alkyl, substituted or unsubstituted aryl, substituted or unsubstituted benzyl;

R$_3$=hydrogen, alkyl, substituted or unsubstituted aryl, substituted or unsubstituted benzyl;

R$_4$=hydrogen, alkyl, substituted or unsubstituted aryl, substituted or unsubstituted benzyl.

* * * * *